(12) United States Patent
Harpman

(10) Patent No.: US 9,442,102 B2
(45) Date of Patent: Sep. 13, 2016

(54) COLORIMETRIC OIL TESTING APPARATUS AND SYSTEM

(71) Applicant: Richard C. Harpman, Poland, OH (US)

(72) Inventor: Richard C. Harpman, Poland, OH (US)

( * ) Notice: Subject to any disclaimer, the term of this patent is extended or adjusted under 35 U.S.C. 154(b) by 0 days.

(21) Appl. No.: 14/696,751

(22) Filed: Apr. 27, 2015

(65) Prior Publication Data

US 2015/0309004 A1   Oct. 29, 2015

Related U.S. Application Data

(60) Provisional application No. 61/985,089, filed on Apr. 28, 2014.

(51) Int. Cl.
| | | |
|---|---|---|
| G01N 21/75 | (2006.01) | |
| G01N 33/28 | (2006.01) | |
| G01N 21/78 | (2006.01) | |
| G01N 21/84 | (2006.01) | |
| G01N 21/80 | (2006.01) | |

(52) U.S. Cl.
CPC .......... *G01N 33/2888* (2013.01); *G01N 21/78* (2013.01); *G01N 21/8483* (2013.01); *G01N 21/80* (2013.01)

(58) Field of Classification Search
CPC ............ G01N 21/78; G01N 33/2888; G01N 21/8483; G01N 21/80
See application file for complete search history.

(56) References Cited

U.S. PATENT DOCUMENTS

| | | |
|---|---|---|
| 2,770,530 A | 11/1956 | Bergstrom et al. |
| 3,580,704 A | 5/1971 | Pickup et al. |
| 2008/0206874 A1* | 8/2008 | Manka ................ G01N 21/78 436/2 |

FOREIGN PATENT DOCUMENTS

GB   WO2012104620   *   8/2012

* cited by examiner

*Primary Examiner* — Dennis M White
(74) *Attorney, Agent, or Firm* — Harpman & Harpman

(57) ABSTRACT

A motor vehicle oil quality testing apparatus and system to assess the quality and viability of motor oil in a vehicle to determine if a change of oil is needed. An absorbent strip of chemically treated material is mounted on a self-contained single use display and test card on which a used oil sample is deposited and will change color based on the oil's determined alkalinity in a sealable color comparison chamber indicated to the user if the oil should be changed.

7 Claims, 2 Drawing Sheets

COLORIMETRIC OIL TESTING APPARATUS AND SYSTEM

This application claims the benefit of U.S. Provisional Application No. 61/985,089, filed Apr. 28, 2014.

BACKGROUND OF THE INVENTION

1. Technical Field

This invention related to colorimetric indicators, more particularly to pH colorimetric indicators which are chemical substances that change color over a given pH range and the user application apparatus to contain same.

2. Description of Prior Art

Prior art testing systems to determine the quality of motor oil have been developed in which the pH of the oil indicates the level of contaminants which relate directly to wear issues in the engine. Modern lubricating oil has a hydrocarbon base and a variety of chemical additives to enhance the oil effectiveness and cleaning abilities. Typically, such additives impart alkalinity to the oil over time when the oil becomes contaminated with insoluble and soluble contaminants including acidic oxidation products. Examples of such prior art chemically treated test strip materials for determining the effective pH and therefore quality of the oil can be seen in U.S. Pat. Nos. 2,770,530 and 3,580,704.

SUMMARY OF THE INVENTION

An oil quality testing apparatus that allows users to determine their engine oil quality as to continued use or required change in an automobile application. The testing device utilizes a chemically reactive test strip mounted in a single use analysis and display holder providing an oil dipstick enabled oil deposit thereon in an isolation viewing chamber for the visual indication of oil chemical reaction by a color change to determine if an oil change is required based on oil quality.

DETAILED DESCRIPTION OF THE INVENTION

Figure 1:
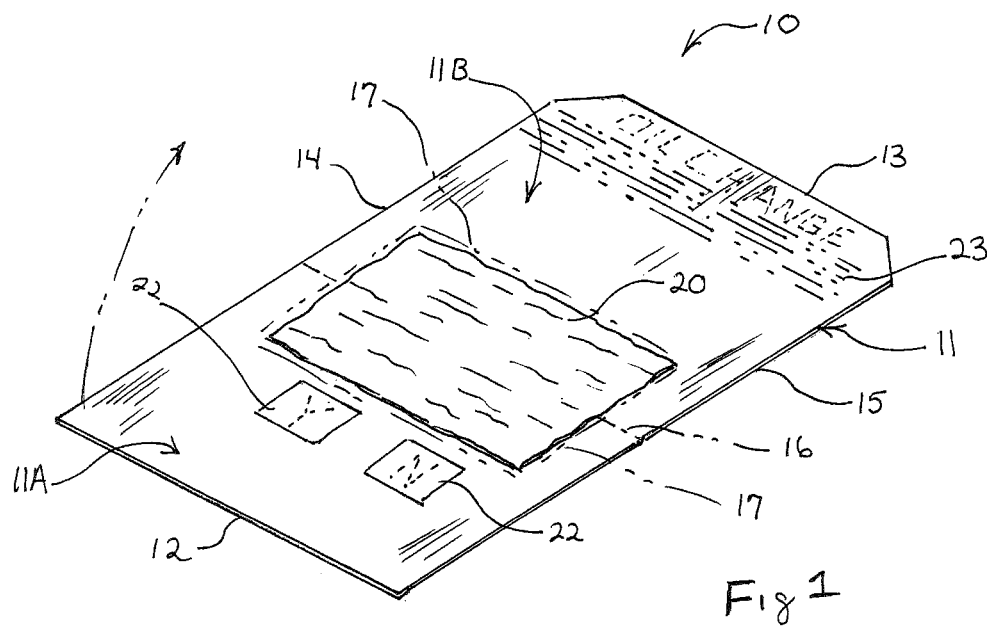
FIG. 1 is a perspective view of the oil quality testing device of the invention prior to use.

An oil quality testing apparatus 10 of the invention can be seen in FIG. 1 of the drawings to provide for a direct chemical analysis of lubricating engine oil quality. The testing apparatus 10 is comprised of a test strip carrier 11 formed of a thin, flat, flexible material such as synthetic resin sheet or the like. The test strip carrier 11 has, in this example, oppositely disposed end edges 12 and 13 and interconnecting spaced parallel elongated side edges 14 and 15. The test strip carrier 11 has a transverse fold line 16 midway between its respective end edges 12 and 13 to designate and affect for ease of manual folding there along defining two opposing surface areas 11A and 11B as will be disclosed and described in greater detail hereinafter.

Figure 3:
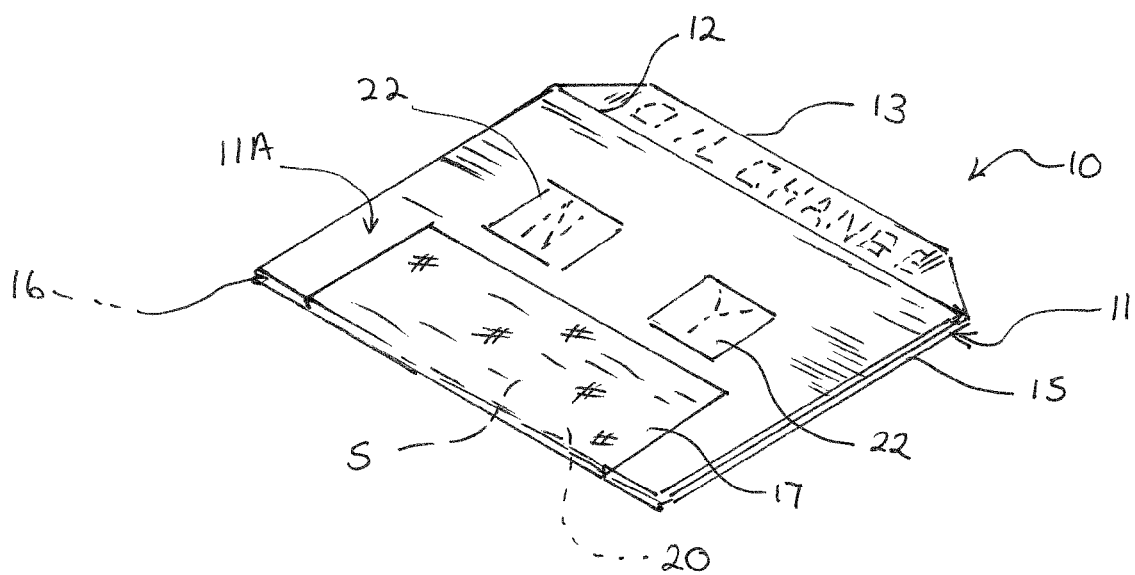
FIG. 3 is a perspective view of the oil quality testing device closed and sealed after oil deposit showing test results.

A transparent viewing window 17 is formed along and extends translaterally from the fold line 16 in spaced relation to the respective side and end edges 14, 15, 12 and 13 respectively, thus defining a continuous overlapping surface engagement perimeter about the window 17 when the test strip carrier 11 is folded there along engaging the test strip area 11A over and onto the test strip area 11B as seen in FIG. 3 of the drawings during test evaluation as will be described.

An oil test strip 20 of chemically treated absorbent material is affixed over and onto the transparent viewing window 17 which will allow the test strip 20 to be viewed when captured within the folded engaged and sealed test strip carrier 11.

The test strip 20 is defined as an acid base indicator composition for testing lubricating oils by determining the effective concentration of acid contaminants so indicated by color change to determine if the vehicle's oil needs to be changed.

An example of such testing indication material can be seen in U.S. Pat. No. 2,770,530 which is incorporated by reference disclosing an indicator developer solution compound to treat a strip of absorbent material, an example which can be seen as including, but not limited to:

|  | Percent by volume |
|---|---|
| Ethanol (containing 5% v. water) | 32.0 |
| 4-methyl-2-pentanol | 17.0 |
| Petroleum solvent (about 65% w. aromatics, approx. Boiling range, 238 to 312° F.) | 25.2 |
| Methylnaphthalene | 25.0 |
| Glycerol | 0.8 |
| Indicator dissolved in above developer solution | |
| Bromocresol green | 57 mg./100 cc. of solution |
| Naphthyl red (S.A.) (4-amino-1-naphthaleneazobenzene-4'-sulphonic acid). | 67 mg./100 cc. of solution |
| Inorganic base to adjust indicator-developer solution To neutrality | |
| Sodium hydroxide in ethanol (0.1 0.8 ml.) | To neutrality (about normal) |

The above illustration of color indicator developer solution formulation when used to treat an indicator sheet of material having uniform absorptive properties of a neutral or white color. Such examples may include and are known in the art as analytical filter paper, such as brand name Waterman's 4, .2 or .1.

The indicator solution for viability in the test strip 20 utilized in the invention are preferred indicators that develop a strong readily identifiable reaction color and remain stable for immediate visual inspection and review by the user.

The test strip carrier 11 has a single or multiple color test comparison indicia 22 printed on their reverse surface of the test strip carrier 11 adjacent the viewing window 17 which overlies the treated test strip 20 when folded as hereinbefore described and seen in FIG. 3 of the drawings.

The test strip carrier 11 may have a pressure sensitive adhesive 23 applied thereto for retaining the folded test strip carrier 11, perspective areas 11A and 11B together after the oil sample has been deposited on the test strips 20 in the following application test utilization sequence example.

Figure 2:
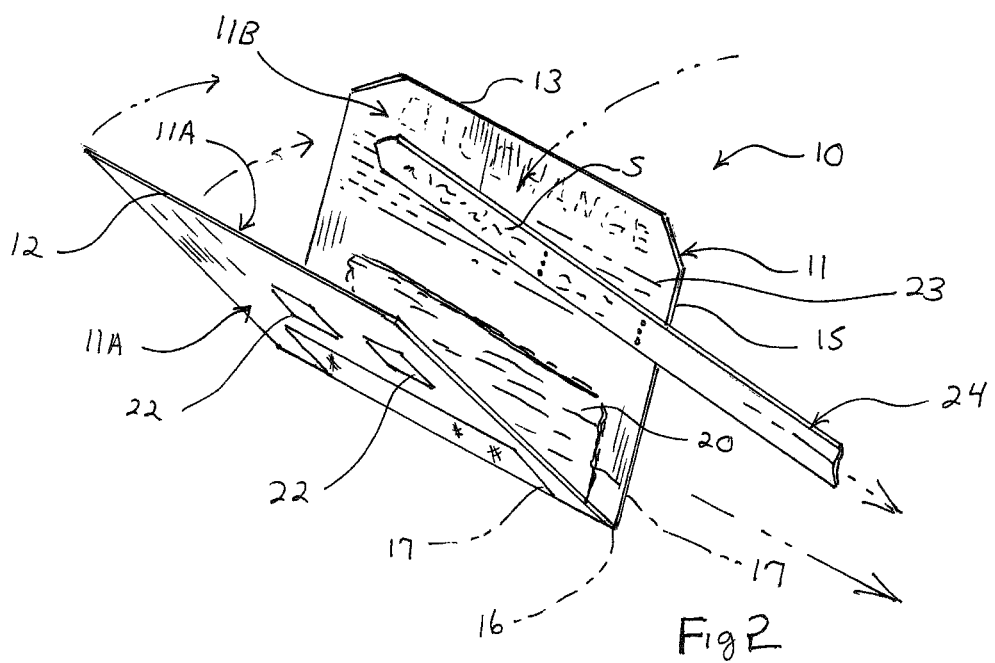
FIG. 2 is a perspective view of the oil quality testing device in use with an oil dipstick representation positioned to be engaged therewithin.

In use, an engine oil level dipstick 24 is removed from the engine (not shown) as to typically check the engine's oil level functioning as a standard measuring apparatus. The oil level dipstick 24 is then drawn between and across the test strip 20 on the test strip carrier 11 which is partially folded to receive same as seen in FIG. 2 of the drawings along the fold line 16 which as noted intersects the material test strip 20 and the viewing window 17 as hereinbefore described. A dipstick 24 is drawn through and against a folded test strip 20 depositing an oil sample S on the absorbent test strip while simultaneously cleaning the dipstick as is well known and understood by those in the art.

The folded test strip carrier 11 adheres together isolating the oil impregnated test strip 20 from the user. It will be evident that the position of the color test comparison indicia 22 next to the viewing window 17 when folded allows for a simple clear and easy comparison to the color of the test strip 20 which changes upon reaction with the oil as to the oil's alkaline contamination and therefore an indication of its quality.

In this example, contaminated oil will change the test strip 20 to red which indicates the oil should be changed illustrated by the Y (red color). Conversely less contaminated oil would register green as indicated by N (green color) denoting that no oil change is needed at this time.

It will be seen that from the above description that the test strip carrier 11 may alternately be completely transparent with the test comparison color imprinted and applied thereon and the viewing window being integral to the card body itself and thus a designated area defined by the test strip becomes the viewable port when folded and sealed as previously described.

It will thus be seen that a new and novel oil quality testing apparatus and system has been illustrated and described and it will be apparent to those skilled in the art that various changes and modification may be made thereto without departing from the spirit of the invention.

Therefore I claim:

1. A test strip carrier and display for an oil testing strip comprises in combination,
   a thin base sheet of non-porous support and display material,
   a transparent central viewing portion of said base sheet,
   an oil test strip secured on said transparent central viewing portion of said base sheet,
   at least one color test comparison surface on said base sheet adjacent said transparent central viewing portion,
   an adhesive on a portion of said base sheet inwardly from an edge of said base sheet in spaced relation to said oil test strip,
   a base sheet fold line extending transversely across said test strip and said transparent viewing portion of said base sheet.

2. The test strip carrier and display for an oil testing strip set forth in claim 1 wherein said base sheet is of synthetic resin film.

3. The test strip carrier and display for an oil testing strip set forth in claim 1 wherein said oil test strip comprises,
   a chemically treated absorbent material of an acid based indicator composition by determining the concentration of acid contents in the oil indicated by color change of said oil test strip.

4. The test strip carrier and display for an oil testing strip set forth in claim 1 wherein said color test comparison surfaces comprises,
   a color printed on the base sheet surface in oppositely disposed adjacent relation to said oil test strip.

5. The test strip carrier and display for an oil testing strip set forth in claim 1 wherein said oil test carrier and display when folded on said fold line captures and isolates oil said test strip within said non-porous base sheet for viewable display.

6. The test strip carrier and display for an oil testing strip set forth in claim 1 wherein said adhesive on a portion of said base sheet comprises,
   a pressure sensitive adhesive for selective engagement and retainment of the adjacent surface portion of said base sheet when folded there against.

7. The test strip carrier and display for an oil testing strip set forth in claim 1 wherein said color test comparison surface area further comprises,
   indicia on said color test surfaces.

* * * * *